(12) United States Patent
Jia

(10) Patent No.: US 11,460,387 B2
(45) Date of Patent: Oct. 4, 2022

(54) BENDING TEST DEVICE OF FLEXIBLE DISPLAY PANEL

(71) Applicant: WUHAN CHINA STAR OPTOELECTRONICS SEMICONDUCTOR DISPLAY TECHNOLOGY CO., LTD., Hubei (CN)

(72) Inventor: Chengjie Jia, Hubei (CN)

(73) Assignee: WUHAN CHINA STAR OPTOELECTRONICS SEMICONDUCTOR DISPLAY TECHNOLOGIES CO., LTD., Hubei (CN)

( * ) Notice: Subject to any disclaimer, the term of this patent is extended or adjusted under 35 U.S.C. 154(b) by 140 days.

(21) Appl. No.: 16/616,077

(22) PCT Filed: May 22, 2019

(86) PCT No.: PCT/CN2019/087934
§ 371 (c)(1),
(2) Date: Nov. 22, 2019

(87) PCT Pub. No.: WO2020/124951
PCT Pub. Date: Jun. 25, 2020

(65) Prior Publication Data
US 2021/0333183 A1    Oct. 28, 2021

(30) Foreign Application Priority Data

Dec. 18, 2018  (CN) .......................... 201811554695.2

(51) Int. Cl.
*G01N 3/20* (2006.01)
*G01N 3/02* (2006.01)
*G09F 9/30* (2006.01)

(52) U.S. Cl.
CPC ................ *G01N 3/20* (2013.01); *G01N 3/02* (2013.01); *G01N 2203/0023* (2013.01); *G09F 9/301* (2013.01)

(58) Field of Classification Search
CPC ............ G01N 3/34; G01N 2203/0264; G01N 2203/0023; G01N 2203/0005; G01N 3/08;
(Continued)

(56) References Cited

U.S. PATENT DOCUMENTS 3,286,516 A * 11/1966 Post .......................... G01N 3/20
73/853
8,544,340 B1 * 10/2013 Ardelean ................. G01N 3/20
73/849
(Continued)

FOREIGN PATENT DOCUMENTS

CN    106596078 A    4/2017
CN    106783660 A    5/2017
(Continued)

*Primary Examiner* — Brandi N Hopkins
(74) *Attorney, Agent, or Firm* — Hauptman Ham, LLP

(57) ABSTRACT

This disclosure relates to flexible display screen testing technology. A bending test device for a flexible display panel is provided. The bending test device includes a first bracket, a second bracket disposed in parallel to a side of the first bracket, and at least two first carriers laminated between the first bracket and the second bracket. Each of the first carriers is configured for bending and carrying a flexible display panel. The bending test for a plurality of flexible display panels can be simultaneously performed by laminating the first carrier.

20 Claims, 3 Drawing Sheets

(58) Field of Classification Search
CPC ... G01N 2203/0617; G01N 2203/0682; G01N 27/22; G01N 2203/0629; G01L 5/0038; G01L 5/0057; G01L 5/0076
See application file for complete search history.

(56) References Cited

U.S. PATENT DOCUMENTS

2012/0067134 A1* 3/2012 Bell .................. G02F 1/133305
73/800
2019/0154555 A1 5/2019 Han et al.

FOREIGN PATENT DOCUMENTS

| | | |
|---|---|---|
| CN | 206601304 U | 10/2017 |
| CN | 206787946 U | 12/2017 |
| CN | 107631861 A | 1/2018 |
| CN | 108593471 A | 9/2018 |
| CN | 108844830 A | 11/2018 |
| CN | 109596439 A | 4/2019 |
| KR | 10-2016-0000925 A | 1/2016 |

* cited by examiner

BENDING TEST DEVICE OF FLEXIBLE DISPLAY PANEL

FIELD OF INVENTION

This disclosure relates to flexible display screen technology, and more particularly, to a bending test device of flexible display panel.

BACKGROUND OF INVENTION

A flexible display device is formed by forming a thin film encapsulation (TFE) and an organic light emitting diode (OLED) device on a flexible substrate, thereby achieving a normal display effect even when folded or bent. The flexible display device has a wide range of application prospects in the field of portable electronic devices and the like. In production of the flexible display device, it is usually required to perform a bending test on the flexible display panel in the flexible display device to detect bending effect of the flexible display panel.

However, the bending test technology of the flexible display panel is not perfect, because material and product testing amount of the bending test device is limited. That is, conventional bending test methods and devices can only test a single flexible display panel, and cannot perform the bending test on a large number (or all) of flexible display panels.

Therefore, it is necessary to provide a bending test device for a flexible display panel that provides a large or batch of flexible display panels for simultaneous bending tests.

SUMMARY OF INVENTION

The disclosure provides a bending test device for a flexible display panel, which effectively solves the technical problem that a conventional bending test device cannot perform a large number of flexible display panels for simultaneous bending tests.

To achieve the above object, the disclosure provides a bending test device for a flexible display panel. The bending test device comprises a first bracket, a second bracket disposed in parallel to a side of the first bracket, and at least two first carriers laminated between the first bracket and the second bracket. Each of the first carriers is configured for bending and carrying a flexible display panel. The flexible display panel includes a first portion, a second portion, and a third portion connecting the first portion and the second portion, the first portion and the second portion are fixed to the first carrier, and the third portion is bent in a first gap of the first carrier. Each of the first carriers comprises a first carrying platform and a second carrying platform, the first carrying platform is connected to the first bracket, and the second carrying platform is connected to the second bracket, a separation interval is disposed between the at least two first carriers.

In an embodiment of the disclosure, the first gap is disposed between the first carrying platform and the second carrying platform.

In an embodiment of the disclosure, a horizontal axis of the third portion of one flexible display panel is not in contact with a horizontal axis of the first portion and the second portion of the other flexible display panel.

In an embodiment of the disclosure, the bending test device further comprises a third bracket disposed in parallel to a side of the second bracket, and at least two second carriers are laminated between the second bracket and the third bracket.

In an embodiment of the disclosure, each of the second carrier has a second gap, and each of the second carrier comprises a third carrying platform and a fourth carrying platform, the third carrier platform is connected to the second bracket, the fourth carrying platform is connected to the third bracket, and the second gap is formed between the third carrying platform and the fourth carrying platform.

In an embodiment of the disclosure, the first carrier further comprises a first extension portion for carrying another flexible display panel.

In an embodiment of the disclosure, the second carrier further comprises a second extension portion, and the second extension portion is adjacent to the second carrying platform for carrying another flexible display panel.

In an embodiment of the disclosure, an anti-slip pad is disposed on the first carrier, and the flexible display panel is disposed on the anti-slip pad to prevent the flexible display panel from slipping.

In an embodiment of the disclosure, an anti-slip pad is disposed on the second carrier, and the flexible display panel is disposed on the anti-slip pad to prevent the flexible display panel from slipping.

In an embodiment of the disclosure, the bending test device further comprises a base and a guide rail disposed on the base. The first bracket is movably disposed on one side of the guide rail, and the second bracket is movably disposed on the other side of the guide rail. The first bracket and the second bracket slide relative to each other along the guide rail during the bending test.

To achieve the above object, the disclosure further provides a bending test device for a flexible display panel. The bending test device comprises a first bracket, a second bracket disposed in parallel to a side of the first bracket, and at least two first carriers laminated between the first bracket and the second bracket. Each of the first carriers is configured for bending and carrying a flexible display panel. The flexible display panel includes a first portion, a second portion, and a third portion connecting the first portion and the second portion, the first portion and the second portion are fixed to the first carrier, and the third portion is bent in a first gap of the first carrier.

In an embodiment of the disclosure, each of the first carriers comprises a first carrying platform and a second carrying platform, the first carrying platform is connected to the first bracket, and the second carrying platform is connected to the second bracket, the first gap is disposed between the first carrying platform and the second carrying platform.

In an embodiment of the disclosure, a separation interval is disposed between the at least two first carriers, a horizontal axis of the third portion of one flexible display panel is not in contact with a horizontal axis of the first portion and the second portion of the other flexible display panel.

In an embodiment of the disclosure, the bending test device further comprises a third bracket disposed in parallel to a side of the second bracket, and at least two second carriers are laminated between the second bracket and the third bracket.

In an embodiment of the disclosure, each of the second carrier has a second gap, and each of the second carrier comprises a third carrying platform and a fourth carrying platform, the third carrier platform is connected to the second bracket, the fourth carrying platform is connected to the third bracket, and the second gap is formed between the third carrying platform and the fourth carrying platform.

In an embodiment of the disclosure, the first carrier further comprises a first extension portion for carrying another flexible display panel.

In an embodiment of the disclosure, the second carrier further comprises a second extension portion, and the second extension portion is adjacent to the second carrying platform for carrying another flexible display panel.

In an embodiment of the disclosure, an anti-slip pad is disposed on the first carrier, the flexible display panel is disposed on the anti-slip pad to prevent the flexible display panel from slipping.

In an embodiment of the disclosure, an anti-slip pad is disposed on the second carrier, the flexible display panel is disposed on the anti-slip pad to prevent the flexible display panel from slipping.

In an embodiment of the disclosure, the bending test device further comprises a base and a guide rail, the guide rail is disposed on the base, and wherein the first bracket is movably disposed on one side of the guide rail, and the second bracket is movably disposed on the other side of the guide rail, the first bracket and the second bracket slide relative to each other along the guide rail during the bending test.

The technical effects are as follows. The disclosure provides a bending test device for a flexible display panel. Bending tests of a large or batch of flexible display panels can be performed simultaneously by laminating a plurality of carriers on the brackets. The drawback that only one flexible display panel can be tested at a time in the conventional bending test device is improved. The test device for the flexible display panel of the disclosure can achieve the effect of performing the bending test for a plurality of flexible display panels simultaneously.

DETAILED DESCRIPTION OF PREFERRED EMBODIMENTS

This description of the exemplary embodiments is intended to be read in connection with the accompanying drawings, which are to be considered part of the entire written description.

Figure 1:
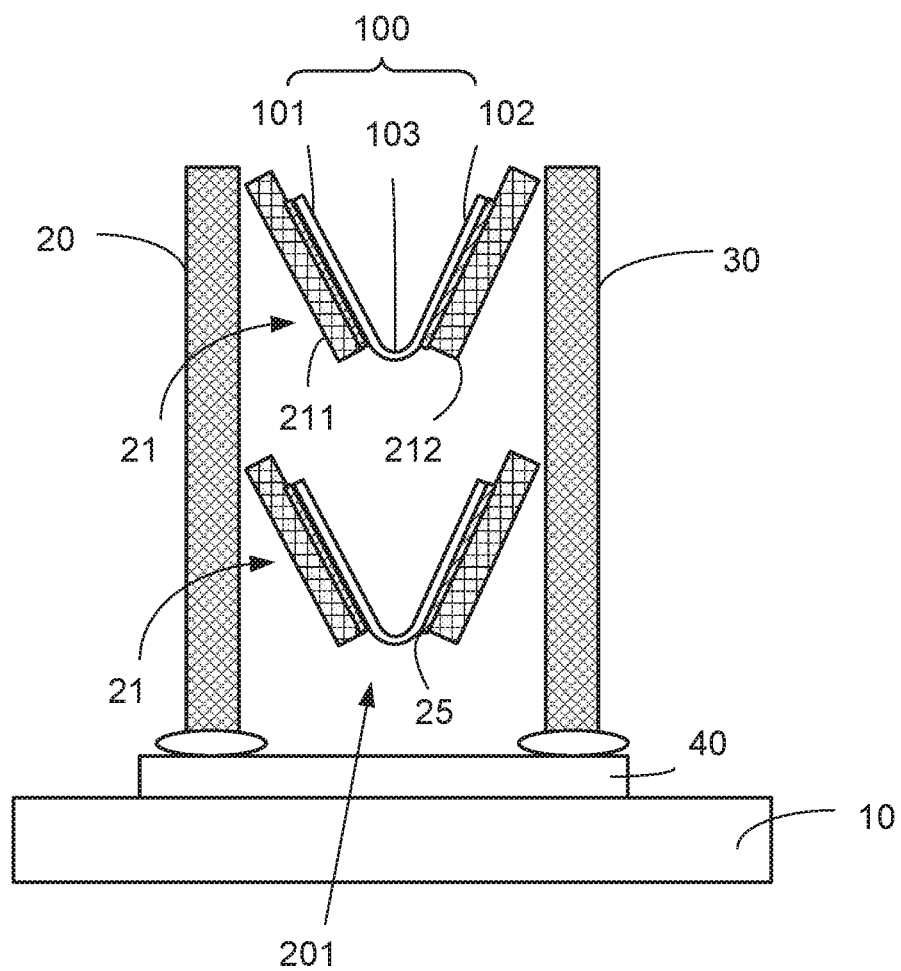
FIG. 1 is a schematic diagram of bending test device for a flexible display panel according to a first embodiment of the disclosure.

Referring to FIG. 1, a schematic diagram of bending test device for a flexible display panel according to a first embodiment of the disclosure is shown. As shown in FIG. 1, the bending test device of the flexible display panel comprises a base 10, a first bracket 20, a second bracket 30, and at least two first carriers 21 that are arranged in a stacked manner.

More specifically, the bending test device of the flexible display panel comprises a first bracket 20, a second bracket 30 disposed in parallel to a side of the first bracket 20, and at least two first carriers 21 laminated between the first bracket 20 and the second bracket 30. Each of the first carriers 21 is configured for bending and carrying a flexible display panel 100. The flexible display panel 100 includes a first portion 101, a second portion 102, and a third portion 103 connecting the first portion 101 and the second portion 102, the first portion 101 and the second portion 102 are fixed to the first carrier 21, and the third portion 103 is bent in a first gap 201 of the first carrier 21.

A guide rail 40 is disposed on the base 10. The first bracket 20 is movably disposed on one side of the guide rail 40, and the second bracket 30 is movably disposed on the other side of the guide rail 40. The first bracket 20 and the second bracket 30 slide relative to each other along the guide rail 40 during performing a bending test. The first bracket 20 and the second bracket 30 are independent of each other.

The flexible display panel 100 is made of a soft material, and is a deformable, flexible display device. The flexible display panel is mainly used for displaying color images, and is combined with a flexible touch panel. The flexible display panel can also be provided with touch functions, and is widely used in portable electronic devices such as mobile phones, tablet computers, and GPS.

Specifically, the flexible display panel 100 includes a first portion 101, a second portion 102, and a third portion 103. The third portion 103 is a bent portion, and the first portion 101 and the second portion 102 are a pair of extended portions. The bent portion is disposed between the pair of extended portions and is connected to the pair of extended portions, respectively. In this embodiment, the flexible display panel 100 is folded by folding the third portion 103, and the bent portion has a circular arc in cross section.

In the first embodiment of the disclosure, each of the first carriers 21 includes a first carrying platform 211 and a second carrying platform 212. The first carrying platform 211 is connected to the first bracket 20, the second bearing platform 212 is connected to the second bracket 30. The first gap 201 is formed between the first carrying platform 211 and the second carrying platform 212.

The first gap 201 between the first carrying platform 211 and the second carrying platform 212 can be adjusted by sliding the two brackets 20, 30. In an initial state, the first carrying platform 211 and the second carrying platform 212 may be close together or may be separated by a certain distance. In this embodiment, the first carrying platform 211 and the second carrying platform 212 are separated by a certain distance in the initial state. The initial state refers to a state in which the flexible display panel 100 is in an untested state, that is, the flexible display panel 100 is not subjected to a force to bend it.

Moreover, the at least two first carriers 21 have a separation interval T (shown in FIG. 2), such that a horizontal axis of the third portion 103 of the flexible display panel 100 is not in contact with a horizontal axis of the first portion 101 and the second portion 102 of the another flexible display panel 100. That is, a sufficient distance is maintained between the two first carriers 21 so that the flexible display panel 100 does not contact with each other during preforming the bending test. In this embodiment, anti-slip pads 25 are disposed on the first carrier and the second carrier, respectively. The flexible display panel 100 is disposed on the anti-slip pad 25 to prevent the flexible display panel 100 from slipping off the first carrier or the second carrier.

Before preforming the bending test, the flexible display panel 100 is disposed on the first carrying platform 211 and the second carrying platform 212, and a portion of the flexible display panel 100 to be tested is aligned and disposed at a position between the first carrying platform 211 and the second carrying platform 212. Then, the flexible display panel 100 is fixed with the first carrying platform 211 and the second carrying platform 212, respectively. At this time, the flexible display panel 100 is not bent and the flexible display panel 100 is in an extended state. The first bracket 20 and the second bracket 30 are away from each other, and a plane of the first carrying platform 211 and a plane of the second carrying platform 212 are both roughly parallel to a plane of the base 10.

During the bending test, the first bracket 20 and the second bracket 30 move toward each other under the driving of the guide rail 40, that is, the first bracket 20 moves along one direction (for example, the right side) of the guide rail 40, and the second bracket 30 moves along another direction (for example, the left side) of the guide rail 40. The first bracket 20 and the second bracket 30 are respectively moved from the side edges toward a middle direction by the guide rails 40, thereby enabling the flexible display panel 100 to be bent. Since two or more first carriers 21 are disposed between the first bracket 20 and the second bracket 30 in a stacked manner, the first carriers 21 are stacked one on another. When the first bracket 20 and the second bracket 30 are moved in an opposite direction, the plurality of flexible display panels 100 respectively disposed on the plurality of first carriers 21 can simultaneously perform the bending test to realize batch bending testing of the flexible display panels.

Figure 2:
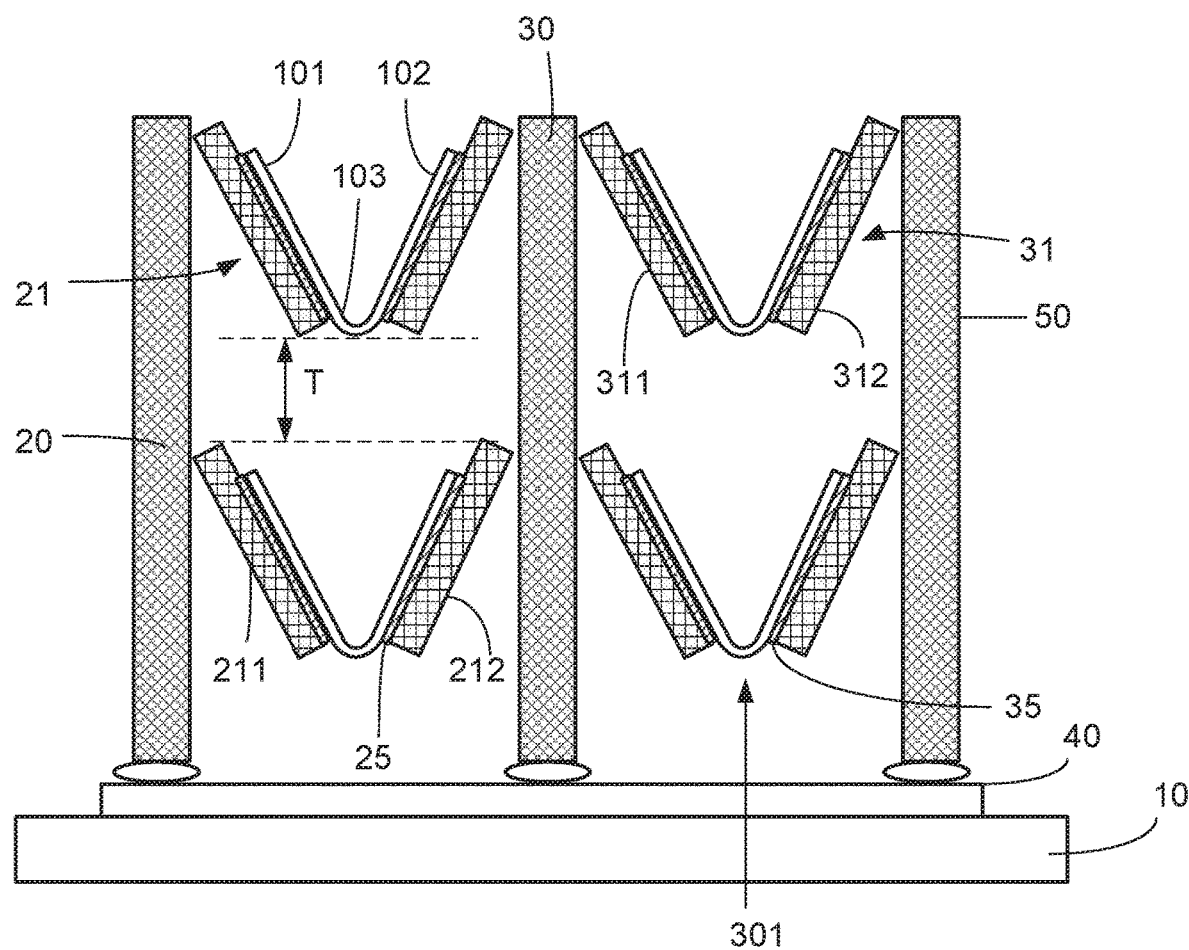
FIG. 2 is a schematic diagram of bending test device for a flexible display panel according to a second embodiment of the disclosure.

Referring to FIG. 2, a schematic diagram of bending test device for a flexible display panel according to a second embodiment of the disclosure is shown. The difference between this embodiment and the first embodiment is that the bending test device of the flexible display panel further includes a third bracket 50 disposed parallel to one side of the second bracket 30, and at least two second carriers 31 are laminated between the second bracket 30 and the third bracket 50.

Each of the second carriers 31 has a second gap 301, and each of the second carriers 31 comprises a third carrying platform 311 and a fourth carrying platform 312. The third carrier platform 311 is connected to the second bracket 30, and the fourth carrying platform 312 is connected to the third bracket 50. The second gap 302 is formed between the third carrying platform 311 and the fourth carrying platform 312. In the present embodiment, the third carrying platform 311 and the fourth carrying platform 312 of the second carrier 31 are provided with a sliding pad 35, respectively. The flexible display panel 100 is disposed on the sliding pads 35, thereby the flexible display panel 100 is prevented from slipping off the third carrying platform 311 and the fourth carrying platform 312.

During the bending test, the first bracket 20 and the second brackets 30 respectively move toward each other under the driving of the guide rail 40, and the third bracket 50 can be horizontally moved by the guide rail 40 toward the second bracket 30. The plurality of flexible display panels 100 on the first carriers 21 and the second carriers 31 can simultaneously perform the bending test to realize batch testing of the flexible display panels.

In more detail, in this embodiment, the first bracket 20 and the third bracket 50 are in a fixed state, and the guide rail 40 drives the second bracket 30 to move horizontally relative to the first bracket 20 and the third bracket 50, respectively. When the guide rail 40 drives the second bracket 30 to move along the direction toward the first bracket 20, the flexible display panel 100 between the first bracket 20 and the second bracket 30 is performed the bending test, and the flexible display panel 100 between the third bracket 50 and the second bracket 30 is deployed. When the guide rail 40 drives the second bracket 30 to move in the direction of the third bracket 50, the flexible display panel 100 between the third bracket 50 and the second bracket 30 is performed the bending test, the flexible display panel 100 between the first bracket 20 and the second bracket 30 is unfolded. Moreover, the longer of bracket lengths of the first bracket 20, the second bracket 30, and the third bracket 50 in the vertical direction, the greater amount of the flexible display panels 100 that can be loaded and subjected to perform the bending test. The greater amount of the first bracket 20, the second bracket 30 and the third bracket 30 in the horizontal direction (for example, the fourth bracket, the fifth bracket, etc. can be included), the greater amount of the flexible display panels 100 that can be loaded and subjected to perform the bending test. The effect of doubling the amount of the flexible display panels 100 that simultaneously perform the bending test can be achieved.

Figure 3:
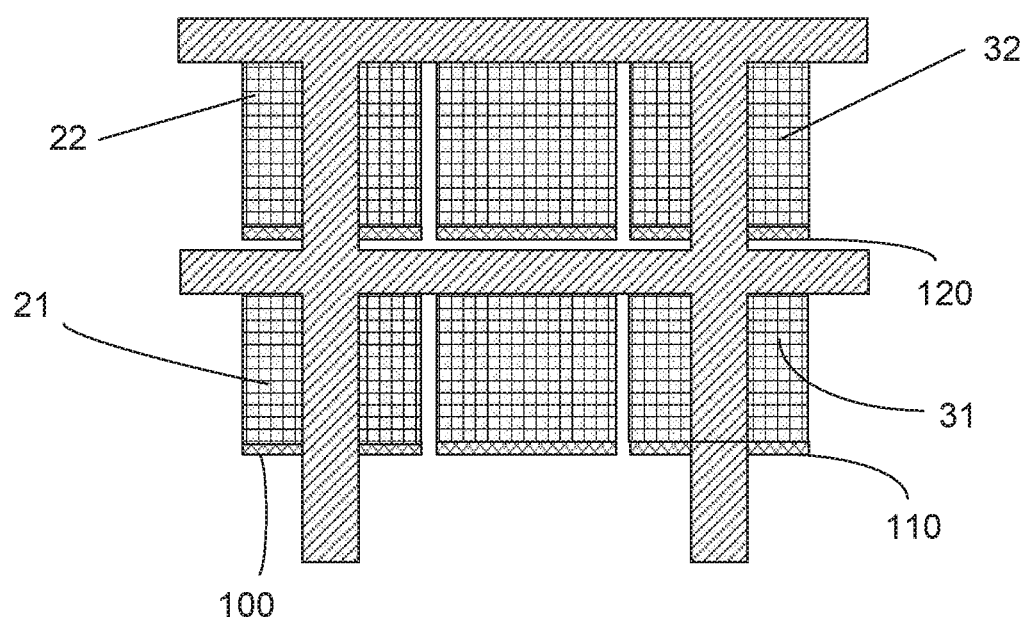
FIG. 3 is a schematic diagram of bending test device for a flexible display panel according to a third embodiment of the disclosure.

Referring to FIG. 3, a schematic diagram of bending test device for a flexible display panel according to a third embodiment of the disclosure is shown. The difference between this embodiment and the first embodiment is that the first carrier 21 further includes a first extension portion 22 for carrying another flexible display panel 110, and the second carrier 31 further includes a second extension portion 32 for carrying another flexible display panel 120.

Furthermore, the principle of this embodiment is that the length or width of the first carrier 21 and the second carrier 31 is increased, so that areas of the first carrier 21 and the second carrier 31 for carrying the flexible display panel 100 is increased. Compared with the foregoing embodiment, the first carrier 21 and the second carrier 31 can be made to dispose more flexible display panels. Thus, the effect that more flexible display panels are performed the bending test simultaneously is further realized.

The technical effects are as follows. The disclosure provides a bending test device for a flexible display panel. Bending tests of a large or batch of flexible display panels can be performed simultaneously by laminating a plurality of carriers on the brackets. The drawback that only one flexible display panel can be tested at a time in the conventional bending test device is improved. The test device for the flexible display panel of the disclosure can achieve the effect of performing the bending test for a plurality of flexible display panels simultaneously.

This disclosure has been described with preferred embodiments thereof, and it is understood that many changes and modifications to the described embodiment can be carried out without departing from the scope and the spirit of the invention.

What is claimed is:

1. A bending test device for a flexible display panel, comprising:
   a first bracket;
   a second bracket disposed in parallel to a side of the first bracket, wherein the second bracket is moveable towards the first bracket; and
   at least two first carriers laminated between the first bracket and the second bracket, each of the first carriers configured for bending and carrying a flexible display panel, wherein the flexible display panel includes a first portion, a second portion, and a third portion connecting the first portion and the second portion, the first portion and the second portion are fixed to the first carrier, and the third portion is bent in a first gap of the first carrier;
   wherein each of the first carriers comprises a first carrying platform and a second carrying platform, the first carrying platform is connected to the first bracket, and the second carrying platform is connected to the second bracket, a separation interval is disposed between the at least two first carriers.

2. The bending test device according to claim 1, wherein the first gap is disposed between the first carrying platform and the second carrying platform.

3. The bending test device according to claim 1, wherein a horizontal axis of the third portion of one flexible display panel is not in contact with a horizontal axis of the first portion and the second portion of the other flexible display panel.

4. The bending test device according to claim 1, further comprising a third bracket disposed in parallel to a side of the second bracket, and at least two second carriers are laminated between the second bracket and the third bracket.

5. The bending test device according to claim 4, wherein each of the second carriers has a second gap, and each of the second carrier comprises a third carrying platform and a fourth carrying platform, the third carrier platform is connected to the second bracket, the fourth carrying platform is connected to the third bracket, and the second gap is formed between the third carrying platform and the fourth carrying platform.

6. The bending test device according to claim 4, wherein the second carrier further comprises a second extension portion, and the second extension portion is adjacent to the second carrying platform for carrying another flexible display panel.

7. The bending test device according to claim 4, wherein an anti-slip pad is disposed on the second carrier, the flexible display panel is disposed on the anti-slip pad to prevent the flexible display panel from slipping.

8. The bending test device according to claim 1, wherein the first carrier further comprises a first extension portion for carrying another flexible display panel.

9. The bending test device according to claim 1, wherein an anti-slip pad is disposed on the first carrier, the flexible display panel is disposed on the anti-slip pad to prevent the flexible display panel from slipping.

10. The bending test device according to claim 1, further comprising a base and a guide rail disposed on the base, and wherein the first bracket is movably disposed on one side of the guide rail, and the second bracket is movably disposed on the other side of the guide rail, the first bracket and the second bracket slide relative to each other along the guide rail during the bending test.

11. A bending test device for a flexible display panel, comprising:
a first bracket;
a second bracket disposed in parallel to a side of the first bracket, wherein the second bracket is moveable towards the first bracket; and
at least two first carriers laminated between the first bracket and the second bracket, each of the first carriers being configured for bending and carrying a flexible display panel;
wherein the flexible display panel includes a first portion, a second portion, and a third portion connecting the first portion and the second portion, the first portion and the second portion are fixed to the first carrier, and the third portion is bent in a first gap of the first carrier.

12. The bending test device according to claim 11, wherein each of the first carriers comprises a first carrying platform and a second carrying platform, the first carrying platform is connected to the first bracket, and the second carrying platform is connected to the second bracket, the first gap is disposed between the first carrying platform and the second carrying platform.

13. The bending test device according to claim 11, wherein a separation interval is disposed between the at least two first carriers, a horizontal axis of the third portion of one flexible display panel is not in contact with a horizontal axis of the first portion and the second portion of the other flexible display panel.

14. The bending test device according to claim 11, further comprising a third bracket disposed in parallel to a side of the second bracket, and at least two second carriers are laminated between the second bracket and the third bracket.

15. The bending test device according to claim 14, wherein each of the second carriers has a second gap, and each of the second carrier comprises a third carrying platform and a fourth carrying platform, the third carrier platform is connected to the second bracket, the fourth carrying platform is connected to the third bracket, and the second gap is formed between the third carrying platform and the fourth carrying platform.

16. The bending test device according to claim 14, wherein the second carrier further comprises a second extension portion, the second extension portion is adjacent to the second carrying platform for carrying another flexible display panel.

17. The bending test device according to claim 14, wherein an anti-slip pad is disposed on the second carrier, the flexible display panel is disposed on the anti-slip pad to prevent the flexible display panel from slipping.

18. The bending test device according to claim 11, wherein the first carrier further comprises a first extension portion for carrying another flexible display panel.

19. The bending test device according to claim 11, wherein an anti-slip pad is disposed on the first carrier, the flexible display panel is disposed on the anti-slip pad to prevent the flexible display panel from slipping.

20. The bending test device according to claim 11, further comprising a base and a guide rail disposed on the base, and wherein the first bracket is movably disposed on one side of the guide rail, and the second bracket is movably disposed on the other side of the guide rail, the first bracket and the second bracket slide relative to each other along the guide rail during the bending test.

\* \* \* \* \*

UNITED STATES PATENT AND TRADEMARK OFFICE
CERTIFICATE OF CORRECTION

PATENT NO. : 11,460,387 B2  
APPLICATION NO. : 16/616077  
DATED : October 4, 2022  
INVENTOR(S) : Chengjie Jia Page 1 of 1

It is certified that error appears in the above-identified patent and that said Letters Patent is hereby corrected as shown below:

On the Title Page

Item (73) should be corrected as follows:  
(73) Assignee: WUHAN CHINA STAR OPTOELECTRONICS SEMICONDUCTOR DISPLAY TECHNOLOGY CO., LTD., Hubei (CN)

Signed and Sealed this  
Sixth Day of June, 2023

Katherine Kelly Vidal  
*Director of the United States Patent and Trademark Office*